(12) United States Patent
Searle

(10) Patent No.: US 6,224,892 B1
(45) Date of Patent: May 1, 2001

(54) POLYESTERHYDROGELS

(75) Inventor: Richard John Searle, Upper Poppleton (GB)

(73) Assignee: Smith & Nephew Plc (GB)

( * ) Notice: Subject to any disclaimer, the term of this patent is extended or adjusted under 35 U.S.C. 154(b) by 0 days.

(21) Appl. No.: 09/380,400

(22) PCT Filed: Feb. 27, 1998

(86) PCT No.: PCT/GB98/00628

§ 371 Date: Oct. 15, 1999

§ 102(e) Date: Oct. 15, 1999

(87) PCT Pub. No.: WO98/38234

PCT Pub. Date: Sep. 3, 1998

(30) Foreign Application Priority Data

Mar. 1, 1999 (GB) .................................................. 9704288

(51) Int. Cl.⁷ .............................. A61F 13/00; C08G 63/02
(52) U.S. Cl. .......................... 424/422; 528/272; 528/300; 528/350; 524/916; 424/443; 424/486
(58) Field of Search ..................................... 528/272, 300, 528/350; 524/916; 424/422, 443, 486

(56) References Cited

U.S. PATENT DOCUMENTS

| | | | |
|---|---|---|---|
| 2,585,323 | * | 2/1952 | Elwell et al. . |
| 3,975,350 | * | 8/1976 | Hudgin et al. . |
| 5,480,963 | * | 1/1996 | Jiang et al. ........................... 528/350 |
| 5,486,444 | * | 1/1996 | Bayley et al. ....................... 430/109 |
| 5,552,453 | * | 9/1996 | Fujita et al. ......................... 522/165 |

FOREIGN PATENT DOCUMENTS

| | | | |
|---|---|---|---|
| 956.583 | * | 2/1950 | (FR) . |
| 1.162.607 | * | 9/1958 | (FR) . |

* cited by examiner

*Primary Examiner*—Samuel A. Acquah
(74) *Attorney, Agent, or Firm*—Larson & Taylor, PLC

(57) ABSTRACT

Novel cross-linked polyesters of pyromellitic anhydride and a polyhydroxy compound containing more than two hydroxyl groups are highly water absorbent, and biodegradable, water swellable. The polyesters may be employed for the manufacture of medical devices such as prosthetic implants, supports for cell cultures or as wound dressings e.g. as a debriding agent.

9 Claims, No Drawings

POLYESTERHYDROGELS

The present invention relates to hydrogels. In particular, the present invention relates to polyester hydrogels and their use as components of medical devices, for example implants and wound dressings.

Linear pyromellitic polyesters, produced by the reaction of pyromellitic anhydride and a diol have been described in U.S. Pat. No. 2,585,323.

We have now surprisingly found that novel cross-linked pyromellitic polyesters, produced by reacting pyromellitic anhydride with a polyol containing more than two hydroxy groups possess properties which make them useful as medical devices.

Thus, according to the invention we provide a polyester comprising residues of pyromellitic acid and a polyol containing more than two hydroxy groups.

The polyesters of the invention are cross-linked and are water swellable hydrogels. By the term a "water swellable hydrogel" is meant a three-dimensional network of a super absorbent polymer which interacts with water or aqueous solutions by swelling and retaining a significant proportion of water within its structure.

For the purpose of this invention a super absorbent polymer is understood to mean a polymer which, when fully hydrated, is capable of having an equilibrium water content of at least 30% w/w.

Aptly, the polyesters of the invention have a number average molecular weight ($M_n$) of greater than 4500, preferably greater than 10,000, and more preferably greater than 20,000.

Any polyols, known per se, containing more than two hydroxy groups are suitable for use in the present invention. Such polyols preferably contain three or more hydroxy groups and include, for example, polyether polyols or polyhydroxyalkanes. Although such polyols are suitable for use in the present invention the invention is not to be considered as being limited to polyether polyols or the polyhydroxyalkanes.

Polyhydroxyalkanes, for use in the present invention, may have from 2 to 6 carbon atoms. Examples of such polyhydroxyalkanes include glycerol, sorbitol, mannitol, adonite, ribite, dulcitol, erythritol and xylite. Polyols such as triols which may be mentioned include trihydroxyalkanes such as glycerol. Mixtures of polyols may also be used.

Examples of polyether polyols also include those sold under the range of TP30 by Perstorp.

The polyesters of the invention may be prepared using conventional methods known per se.

Thus according to the invention we provide a method of manufacturing a polyester as hereinbefore described which comprises reacting pyromellitic anhydride and a polyol containing more than two hydroxy groups at elevated temperature.

The method of manufacturing a polyester according to the invention may optionally include the use of known catalysts.

The ratios of the pyromellitic anhydride and the polyol in the polymerisation reaction will depend upon, inter alia, the functionality of the polyol, that is, the number of free hydroxy groups, the degree of cross-linking required in the resulting polyester and the reactivity of the hydroxy groups. Defined in terms of stoichiometry the ratio of anhydride groups to hydroxy groups should be from 0.7:1 to 1:1.3, preferably 1:1. When a mixture of polyols is used the effective stoichiometry of the polyol may be a fraction.

Polyesters according to the invention may be characterised using conventional techniques known per se, such as infra red spectroscopy, nmr, rheological measurements, glass transition measurements and water uptake.

The polyesters according to the invention are particularly advantageous in that they are biodegradable.

Thus according a further embodiment of the invention there is provided a biodegradable medical device comprising a pyromellitic polyester of the present invention.

Thus the pyromellitic polyesters of the invention may be useful in preparing biodegradable implants such as medical or surgical prostheses, supports for such prostheses, supports for cell cultures such as may be used in ligament, cartilage or tendon repair, sutures, supports for cell cultures in woundcare or as woundcare agents in their own right, eg. debriding agents, pharmaceutical carriers etc. or the copolyesters of the invention may be useful in imaging during interventional procedures.

It is intended that the aforementioned uses should not be limitative and are mentioned by way of example only.

The polyesters of the invention are also advantageous in that they are sterilisable. Any conventional form of sterilisation may be used, eg. steam sterilisation, but an especial benefit of the polyesters of the invention is that they may be sterilised without detrimental effect by gamma-radiation.

Thus according to a further feature of the invention we provide a polyester as hereinbefore described in sterile form, eg. wherein the sterilisation has been carried out by gamma-radiation.

Accordingly, the polyesters of the present invention may be especially useful in wound healing, eg. as a debriding agent.

Thus according to the invention we provide the use of a polyester comprising residues of pyromellitic anhydride and a polyol in the manufacture of a wound healing agent, eg. a debriding agent.

Thus the polyesters and devices of the invention may be applied in a method of wound healing which comprises applying a pyromellitic polyester in accordance with the invention or a device incorporating such a pyromellitic polyester to the wound of a patient.

We especially provide the use of a polyester according to the invention as hereinbefore described.

The invention may now be illustrated but in no way limited by way of example only, and in which temperatures are in degrees celsius.

EXAMPLE 1

Preparation of Polyester from Pyromellitic Dianhydride and TP30 Polyol

Pyromellitic dianhydride (22.00 g, 200 mmol:anhydride) was weighed into a glass jar. TP30 (18.44 g) was added. The mixture was stirred with a spatula to form a white paste. The jar was heated to 110° on an oil bath for 15 mins, with stirring. It was then placed in an oven at 70°. The material was a white paste, roughly the consistency of PVA wood glue. After standing overnight at 70° the material was a greyish-white solid. It was very hard with no signs of tackiness. One piece of the solid was put in deionised water and the other into ethanol (stirred). After 1 hr the piece in water was tacky. The piece in ethanol showed signs of dissolving (visible eddies around its edges). After 2 hrs, the sample in water remained hard with a tacky surface. The sample in ethanol had gone soft and gel-like, and retained its opacity.

Other pieces were put in various solvents each 50 ml of solvent and observed. The results are in Table I.

TABLE I

| Solvent | Sample wt | Observations |
|---|---|---|
| Isopropanol | dry wt 1.66 g | Material became softer. Remained opaque. |
| 5% w/w Sodium Bicarbonate (aqueous) | 0.13 g (dry) @ 2 pm | Frothing observed @ the surface of the polymer. Bits of polymer broke off. Edge of the polymer became gel-like. pH = 8. |
| 0.5% w/w Sodium Hydroxide (aqueous) | 0.94 g (dry) | Eddies observed at the surface of the polymer. |
| PBS | 0.97 g (dry) | Became sticky on the surface. No signs of swelling. |

After 5 days the gel in sodium hydroxide weighed 2.49 g.

EXAMPLE 2

Preparation of Polyester from Pyromellitic Anhydride and TP30 and Glycerol

Pyromellitic anhydride (22.17 g) was mixed with glycerol (13.80 g) and TP30 (4.60 g). They were stirred with a spatula to form a thick white paste. This was put in a silicone paper tray in a glass jar, in an oven at 70°. After 24 hours, the material was a greyish-white viscous liquid which cooled to a brittle solid at room temperature. It became very sticky on standing in air, indicating hygroscopicity. The polymer was soluble in water and ethanol.

EXAMPLE 3

Repeat of Reaction of Example 2 Using Higher Temperature

The components were stirred together to form a thick paste, in a glass jar. The jar was put in an oven at 120°. After 24 hours the polymer was a light brown opaque material, containing small bubbles. It was slightly soft on the surface when hot, though not liquid. When cooled to room temperature it was a hard, brittle solid. It was soluble in 0.5% sodium hydroxide (aq) and it clearly had not gelled.

EXAMPLE 4

Repeat of Reaction of Example 1 Using Higher Temperature

Pyromellitic anhydride (22.00 g) and TP30 (18.45 g) were mixed in a plastic screw-top container to a white paste. The container was put in an oven at 90° and left overnight. The product was a slightly brownish-grey hard solid. It was smashed into pieces about 2 cm cubed and put into 0.1M sodium hydroxide solution. After standing overnight the sodium hydroxide solution had gone to pH5 and was decanted off and replaced with fresh solution. The polymer had shed many small bits, which showed no signs of dissolving. It did not appear to be forming a gel. The polymer appears the same, (ie. no gel). pH=5. The solution was changed again.

After 13 days the polymer appeared gel-like. It was blended in a Moulinex liquidiser to give a paste, it was filtered and washed with phosphate buffered saline (PBS) (70 mm pp mesh).

EXAMPLE 5

Repeat of Reaction of Example 1

Pyromellitic anhydride (22.00 g) was weighed into a glass jar. TP30 (19.00 g) was added, and the two stirred with a spatula to form a white paste. It was heated with stirring or an oil bath at 120° for 15 mins, then put in an oven at 70°. After 24 hours the material was a greyish-brown hard solid. The jar was broken and the pieces of polymer put into 0.1M sodium hydroxide (aq). After 90 mins the edges showed signs of swelling and the pH had increased to 12. After 48 hours the pH had decreased to 4. The material was filtered using 70 $\mu$m pp mesh. The filtrate was reminiscent of a conventional known hydrogel and was put back into solution. Some white lumps were observed. After a further 6 days, the material comprised white lumps plus a small amount of paste-like material. The lumps were liquidised using a Moulinex blender, in 0.1M sodium hydroxide. The pH went from 12 to 4 over 5 mins.

EXAMPLE 6

Repeat of Reaction of Example 4

Pyromellitic anhydride (22.19 g) and TP30 (18.45 g) were mixed to a white paste in a plastic screw-top container. The container was put in an oven at 90° and left overnight. The product was a very hard slightly brownish-grey solid. It was hard to break, but broken into approx 2 cm pieces. Grinding using a) a coffee grinder and b) a ball mill, were attempted. Neither was successful. The ball mill was run for 1 hr a small amount of powder generated. 10 g sodium hydroxide were dissolved in 250 ml water, and mixed with the polymer to pH 14. The polymer was white, and it was observed that the particle size generally seemed smaller than when it was put in the solution. It was filtered, and mixed with 0.1M sodium hydroxide, then blended in a Moulinex liquidiser. The result was a white paste. The pH was measured 10 mins later and found to be 5–6. 1 hr later it was filtered again, and more 0.1M sodium hydroxide added to produce a translucent paste. pH directly after addition of 0.1M sodium hydroxide was 12 to 13.

EXAMPLE 7

Preparation of Hydrogel with Sodium Bicarbonate

Pyromellitic anhydride (22 g) was mixed with TP30 (18 g) and sodium bicarbonate (5 g) in a plastic container to form a white paste. This was sealed and put in an oven at 90°. After 24 hours the material was porous, and had increased in volume by about 2 times. It was a hard greyish-brown solid. It broke into pieces much more easily than previous materials. It was put into 250 ml deionised water. It formed bubbles and the pH went from 8 to 4 in a few minutes. As the particles reacted, they broke up. Further sodium bicarbonate was added. At each addition (about 0.5 to 1 g), bubbling occurred and the material changed to a smooth paste. When addition of aqueous sodium bicarbonate solution produced no more effervescence, 200 ml of PBS was added and the paste left overnight with stirring. The paste was filtered (no.52 filter paper). After 200 ml liquid removed, it was made up to 600 ml with PBS, left to stir for 1 hour and then left to stand for 1 hour. The mixture was filtered again (under the same conditions). The product was a stiff paste (201 g). 60 g PBS added to make a material like smooth wallpaper paste at a pH=7.

EXAMPLE 8

Evaluation of Non-sterile Polyester Hydrogel Paste Using the Gelatine Slab Test

A small, 60 mm diameter, 'Costar' culture dish was used, half filled with 12 ml 40% or 5% gelatine. The gel material was smoothed onto the surface of the gelatine slab to uniform level. The weight increase/decrease of the gelatine slab was then determined, at room temperature, for the 24 hour timepoint only (because of small quantity of sample). The difference was normalised to the initial gelatine slab weight.

Gel slab test.

Water gain by gelatine (% w/w) 40% gelatine:
  Example 7 (non-sterile) 26.2%

Example 7-sterilised
(sterile) 24.8%

Water gain by gelatine (% w/w) 5% gelatine:
  Example 7 (non-sterile) −4.6%

EXAMPLE 9

Repeat of Example 7 With Propylene Glycol

Pyromellitic anhydride (22.21 g), TP30 (18.45 g) and sodium bicarbonate (5.11 g) were mixed to a smooth white paste, and put in an oven in a plastic screw top container at 90° for 16 hours. The polymer had increased its volume about two times and was a greyish hard solid. It was smashed to pieces with a steel implement, then put into 200 ml deionised water, when gas was liberated. Further sodium bicarbonate was added and the mixture made up to 500 ml with deionised water. After the addition of about 15 g sodium bicarbonate, the material had become a paste, made up of small particles. It was left stirring for 3 hours. Filtered until no more liquid dripped from the Buchner funnel (No.52 paper), and the material weighed 243 g. 1 liter of PBS was added, and the mixture was stirred overnight. Stirring was stopped and the paste allowed to settle. It was filtered again, and weighed (263 g). 750 ml fresh PBS was added and stirring was continued. The paste was filtered (No.52 paper) and weighed (312 g). Filtrate added back to paste which was at pH=7 and stirring was continued. Paste filtered and weighed (349 g). pH=7. Filtrate added back. Stirring continued. After 48 hours the paste was filtered and weighed (335 g). The pH was 7. 150 g of paste was mixed with 40 g propylene glycol and 20 ml deionised water to give a smooth paste. 169 g of the paste was mixed with 68 water to also give a paste. 1.0 g of batch was added to 10 ml horse serum in a glass vial. The material remained as a coherent mass. The vial was not shaken, since this would have broken up the gel. The vial was left, and re-examined after 24 hours. No visible change had occurred.

EXAMPLE 10

Further Repeat of Example 7

Pyromellitic anhydride (22.31 g), TP30 (18.45 g) and sodium bicarbonate (5.01 g) were mixed to a smooth white paste, and put in an oven in a plastic screw-top container at 90°. The polymer was removed as a white, porous, hard solid. It was crushed with a steel bar, then added to 500 ml deionised water. The lumps of polymer floated and frothed. 17.0 g sodium bicarbonate were added. Further frothing occurred, and the polymer broke into small pieces. It was subjected to 30 seconds in a Moulinex blender. It was then poured back into the beaker, washing out the blender with 50 ml deionised water. This was added, and the slurry left stirring using a magnetic stirrer at pH=7. After 72 hours the slurry was filtered to give a smooth paste. 100 g of this were reserved for washing with endotoxin-free PBS for an in-vivo study. The paste was stirred in endotoxin-free PBS under aseptic conditions in a laminar flow cabinet and then filtered using 70 μm polypropylene mesh, and put back (stirring) in fresh endotoxin-free PBS. The paste was filtered, and put into foil sachets (1×25 g, 4×10 g) and submitted for gamma-sterilisation.

EXAMPLE 11

Sterilisation

Sterilisation by γ-irradiation (30.1 kGy) did not affect the performance on the gelatin slab test (as shown in Example 8) on the material of Example 10.

Other tests on sterile and non-sterile samples from the same batch were carried out as part of a shelf-life study. The results are shown in Table II.

TABLE II

| Sterile/ | Solids Content | Total ROE* | pH of Extracts | |
| --- | --- | --- | --- | --- |
| Non-sterile | % w/w | % w/w | 1st | 2nd |
| Non-sterile | 6.23 | 13.4 | 7.3 | 7.2 |
| Sterile | 6.27 | 17.0 | 7.3 | 7.4 |

*Residue on evaporation (ROE) is expressed as % w/w per gramme of prepolymer (based on mean solids content).

The only significant observed change on sterilisation was a slight increase in extractable material.

On visual inspection, both the sterile and non-sterile materials were translucent pastes and no apparent change occurred on gamma-sterilisation.

What is claimed is:

1. A cross-linked water-swellable polyester comprising residues derived from pyromellitic acid and a polyol containing more than two hydroxyl groups, and capable of an equilibrium water content of at least 30% w/w.

2. A polyester according to claim 1 having a number average molecular weight ($M_n$) of greater than 4500.

3. A polyester according to claim 1 comprising residues derived from a polyhydroxy alkane or a polyester polyol.

4. A polyester according to claim 1 wherein the ratio of residues derived from pyromellitic acid to those from a polyol is from 0.7:1 to 1:1.3, and the number average molecular weight ($M_n$) is greater than 10,000.

5. A biodegradable medical device comprising the pyromellitic polyester according to claim 1.

6. A device as claimed in claim 5 in the form of an implant, a prosthesis, a support for a cell culture or a wound dressing.

7. A hydrogel comprising a polyester of pyromellitic acid and a polyol containing more than two hydroxy groups according to claim 1.

8. A biodegradable medical device comprising a hydrogel according to claim 7.

9. A biodegradable medical device according to claim 8 in the form of an implant, prosthesis, support for a cell culture or wound dressing.

\* \* \* \* \*